(12) United States Patent
Lenderink et al.

(10) Patent No.: US 6,736,832 B2
(45) Date of Patent: May 18, 2004

(54) METHOD OF OPTIMIZING THE USE OF A TANNING-RELATED DEVICE, DEVICE FOR PERFORMING SUCH A METHOD, AND TANNING-RELATED DEVICE

(75) Inventors: Egbert Lenderink, Eindhoven (NL); Theodorus Johanna Maria Schoenmakers, Eindhoven (NL)

(73) Assignee: Koninklijke Philips Electronics N.V, Eindhoven (NL)

( * ) Notice: Subject to any disclaimer, the term of this patent is extended or adjusted under 35 U.S.C. 154(b) by 129 days.

(21) Appl. No.: 09/897,330

(22) Filed: Jul. 2, 2001

(65) Prior Publication Data

US 2002/0022868 A1 Feb. 21, 2002

(30) Foreign Application Priority Data

Jul. 3, 2000 (EP) .............................. 00114255

(51) Int. Cl.[7] .................................. A61N 5/00
(52) U.S. Cl. .......................... 607/88; 128/898; 600/407
(58) Field of Search ..................... 250/372; 128/898; 607/88–95; 600/407

(56) References Cited

U.S. PATENT DOCUMENTS

| | | | | |
|---|---|---|---|---|
| 4,010,372 A | * | 3/1977 | Adler et al. ................ | 250/372 |
| 4,348,664 A | * | 9/1982 | Boschetti et al. ........... | 340/600 |
| 4,423,736 A | * | 1/1984 | DeWitt et al. ............... | 600/306 |
| 4,428,050 A | * | 1/1984 | Pellegrino et al. .......... | 250/372 |
| 4,535,244 A | * | 8/1985 | Burnham .................... | 250/372 |
| 4,882,598 A | * | 11/1989 | Wulf ....................... | 250/338.1 |
| 4,962,910 A | * | 10/1990 | Shimizu .................... | 250/372 |
| 5,374,825 A | * | 12/1994 | Doty et al. ................ | 250/372 |
| 5,683,437 A | * | 11/1997 | Doty ....................... | 607/91 |
| 5,995,862 A | * | 11/1999 | Gallorini .................. | 600/407 |
| 6,348,694 B1 | * | 2/2002 | Gershteyn et al. .......... | 250/372 |

FOREIGN PATENT DOCUMENTS

| | | | | |
|---|---|---|---|---|
| EP | 0238574 B1 | 9/1987 | | |
| GB | 2236182 A | * | 3/1991 | ............. G01J/1/42 |

OTHER PUBLICATIONS

Minimum erythema dose determination in individuals of skin type V and VI with diffuse reflectance spectroscopy, Kollias, Baqer and Sadiq, Photodermatol Photoimmunol Photomed, Dec. 1994.*

Prediction of Minimal erythema dose with a reflectance melanin meter, Damian et al, British Journal of Dermatology, May 1997.*

Spectral Reflectance of Human Skin in Vivo, Andersen et al, Photodermatol Photoimmunol Photomed, Feb. 1990.*

* cited by examiner

Primary Examiner—Roy D. Gibson
Assistant Examiner—Henry M. Johnson, III
(74) Attorney, Agent, or Firm—Ernestine C. Bartlett

(57) ABSTRACT

Method comprising steps of: A) determining a quantity related to a person's personal minimum erythema dose (MED), B) using said quantity as an input for a tanning-related device, thus influencing its operation, and comprising for the purpose of step A), C) non-invasively measuring a feature of the person's skin related to the person's personal MED, and D) electronically deducing the person's personal MED from the measured feature. Furthermore, a device for use with a tanning-related device (12) comprising measuring means (1) for non-invasively measuring a feature of the person's skin (3) related to the person's personal MED, deduction means (5) for deducting the person's personal MED from the measured feature, and communication means (7) for electronically communicating a signal representing the deduced MED to a tanning-related device. Thus, it is possible to use information coming from an objective measurement for controlling a tanning-related device with no risk of skin damage.

8 Claims, 3 Drawing Sheets

METHOD OF OPTIMIZING THE USE OF A TANNING-RELATED DEVICE, DEVICE FOR PERFORMING SUCH A METHOD, AND TANNING-RELATED DEVICE

BACKGROUND OF THE INVENTION

The invention relates to a method comprising the steps of:

A) determining a quantity related to a person's personal minimum erythema dose (MED), and B) using said quantity as an input for a tanning-related device, thus influencing its operation.

Tanning is induced by irradiation with ultraviolet (UV) light, either from natural sunlight or from a solarium. As is known, large doses of ultraviolet light are harmful. However, the dose that is harmful differs from one person to the next and even from one time to another for a single person.

The parameter currently used to quantify a person's sensitivity to ultraviolet light is the minimum erythema dose (MED), the smallest dose that induces visible redness of the skin. In order to avoid radiation damage, it is generally accepted that this MED should not be exceeded. For efficient tanning, on the other hand, a person wants as high a dose of ultraviolet light as possible. The problem is that the person does not know his MED exactly. Currently, MED can be estimated or measured.

Estimation of MED makes use of the skin type classification (types I–VI, where the users of solaria will almost exclusively fall into types II–IV). Skin type classification is based on visual inspection and on a questionnaire with questions about personal sunburn and tanning experiences. However, substantial errors can be made, and often the skin type cannot be established unambiguously. Because of this uncertainty, it is always advised to stay on the safe side. Many people will therefore start their tanning programs sub-optimally, i.e. with doses that are lower than what they could safely receive.

Measurement of MED involves exposing a series of small patches of skin to increasing doses of ultraviolet light. The lowest dose that induces visible redness is the MED. This measurement is very reliable, but inevitably involves radiation damage to the skin. It is unpleasant, should not be performed repeatedly on the same person, and must always be carried out by a dermatologist. For this reason, such measurements are only suitable for medical purposes and not for use with consumer products.

It has been discovered that a relatively accurate correlation between non-invasively determinable features of the skin and MED exists, as disclosed by L. S. Matchette of the Center for Devices and Radiological Health, of the US Food & Drug Administration, at the 13$^{th}$ International Congress on Photobiology in San Francisco, Calif. By using this correlation one can predict a person's MED without inducing damage to the skin. Thus, there is no objection to repeated measurements by a non-schooled user. The invention aims at benefiting from the advantages offered by this kind of non-invasive determination of a person's personal MED.

OBJECTS AND SUMMARY OF THE INVENTION

According to the invention, this is achieved by a method comprising, for the purpose of step A), the steps of:

C) non-invasively measuring a feature of the person's skin related to the person's personal MED, and D) electronically deducing the person's personal MED from the measured feature.

According to this method it is possible to use information coming from an objective measurement with no risk of skin damage for controlling a tanning-related device. The tanning-related device to which the output signal is provided could be, for example a dosimeter, for example as part of a solar watch, which measures overall light intensity and warns the user when he has probably received a too high sunlight dose. Another suitable tanning-related device is a solarium, which could be switched off automatically when the person has reached his MED.

Advantageously, the light attenuation in the skin is measured during step C). It has been discovered that a relatively good correlation between said attenuation and MED exist.

The light attenuation in the skin can be measured by using optical coherence tomography, which is an imaging technique which is known per se by those skilled in the art, based on low-coherence interferometry, which technique can also be used for the measurement of the light attenuation. The principle of optical coherence tomography is described, for example, in D. Huang et al., "Optical Coherence Tomography", Science 254, 1178 (1991), and optical coherence domain reflectometry is described in B. L. Danielson and C. D. Whittenberg, "Guided Wave Reflectometry With Micrometer Resolution", Appl. Opt. 26, 2836 (1987). The clear advantage of OCDR over OCT for the purpose of the invention is that it is a simpler and cheaper technique.

Besides light having a wavelength at or near 670 nm, as disclosed by L. S. Matchette of the Center for Devices and Radiological Health, of the US Food & Drug Administration, at the 13$^{th}$ International Congress on Photobiology in San Francisco, Calif., light having a wavelength of 1300 nm also appears to be suitable for use with the above-mentioned optical techniques. Since the latter wavelength is also used in the ICT sector, there is no or only a limited need for developing suitable optical components.

It is further possible to use spatially resolved diffuse reflectance spectroscopy which is described, for example, in J. T. Bruulsema et al., "Correlation between Blood Glucose Concentration in Diabetics and Noninvasively Measured Tissue Optical Scattering Coefficient", Opt. Lett. 22, 190 (1997).

Alternatively, the light reflection of the skin is measured during step C), since also the light reflection is correlated with the MED as described in EP 0 238 574 B 1. However, the correlation between the light reflection of the skin and MED appears to be less accurate than the correlation between the light attenuation in the skin and MED. By combining the knowledge of the correlation between the light reflection of the skin and MED and the correlation between the attenuation of the skin and MED it is possible to predict the MED even more accurately. The accuracy of the determination of the MED is expected to increase even further when the measurement is combined with other measured parameters that are known to correlate with the skin's UV sensitivity, such as pigmentation and epidermal thickness. These parameters can also be measured non-invasively.

Preferably, a safe sunbathing time is electronically calculated on the basis of the deduced MED and of a relevant, preferably measured, solar UV radiation level. Information about the electronically calculated safe sunbathing time may be used by a user of a tanning-related device in order to maximize his tanning without the risk of inducing visible redness of the skin.

Another use of the electronically calculated safe sunbathing time may be the automatic turning-off of a solarium as soon as a time period has elapsed corresponding to the safe sun-bathing time since the moment the solarium was turned on.

Another advantageous possible use may be with a dosimeter, for example a solar watch, which measures the solar UV radiation level and warns the user of the dosimeter with a signal as soon as the user's personal MED has been reached, in other words when the safe sunbathing time has elapsed.

According to another aspect of the present invention, a device is provided for use with a tanning-related device.

As indicated above, tanning-related devices, such as solaria, are operated in practice on the basis of an estimated classification of the user's skin type, which has all the disadvantages mentioned above. It is therefore an object of the invention to provide a device which objectively, accurately, and non-invasively gives a user of a tanning-related device information about his MED.

According to a second aspect of the present invention, a device for use with a tanning-related device is provided comprising measuring means for non-invasively measuring a feature of the person's skin related to the person's personal MED, deduction means for deducing the person's personal MED from the measured feature, and communicating means for electronically communicating a signal representing the deduced MED to a tanning-related device.

Advantageously, the device is provided with a timer for giving a warning signal, for instance a sound or light signal, as soon as a time period corresponding to the safe sunbathing time has elapsed. This allows the user of the device to relax fully without worrying that he will develop visible skin redness, because he will be warned just before this would occur.

According to a third aspect of the present invention, a tanning-related device, for example a solarium, comprising a device as described above is provided. This has the clear benefit that the user of the tanning-related device always has at his disposal the possibility of accurately and non-invasively determining his MED which gives him the benefits as described above.

By providing a tanning-related device with a switch which can start a timer and at the same time the tanning-related device itself, and which furthermore switches off the tanning-related device upon receipt of a warning signal of the timer as soon as the safe sunbathing time has elapsed, there will be no risk of his skin becoming red.

BRIEF DESCRIPTION OF THE DRAWING

The invention will be described with reference to the drawings, in which.

DESCRIPTION OF THE PREFERRED EMBODIMENTS

Figure 1:
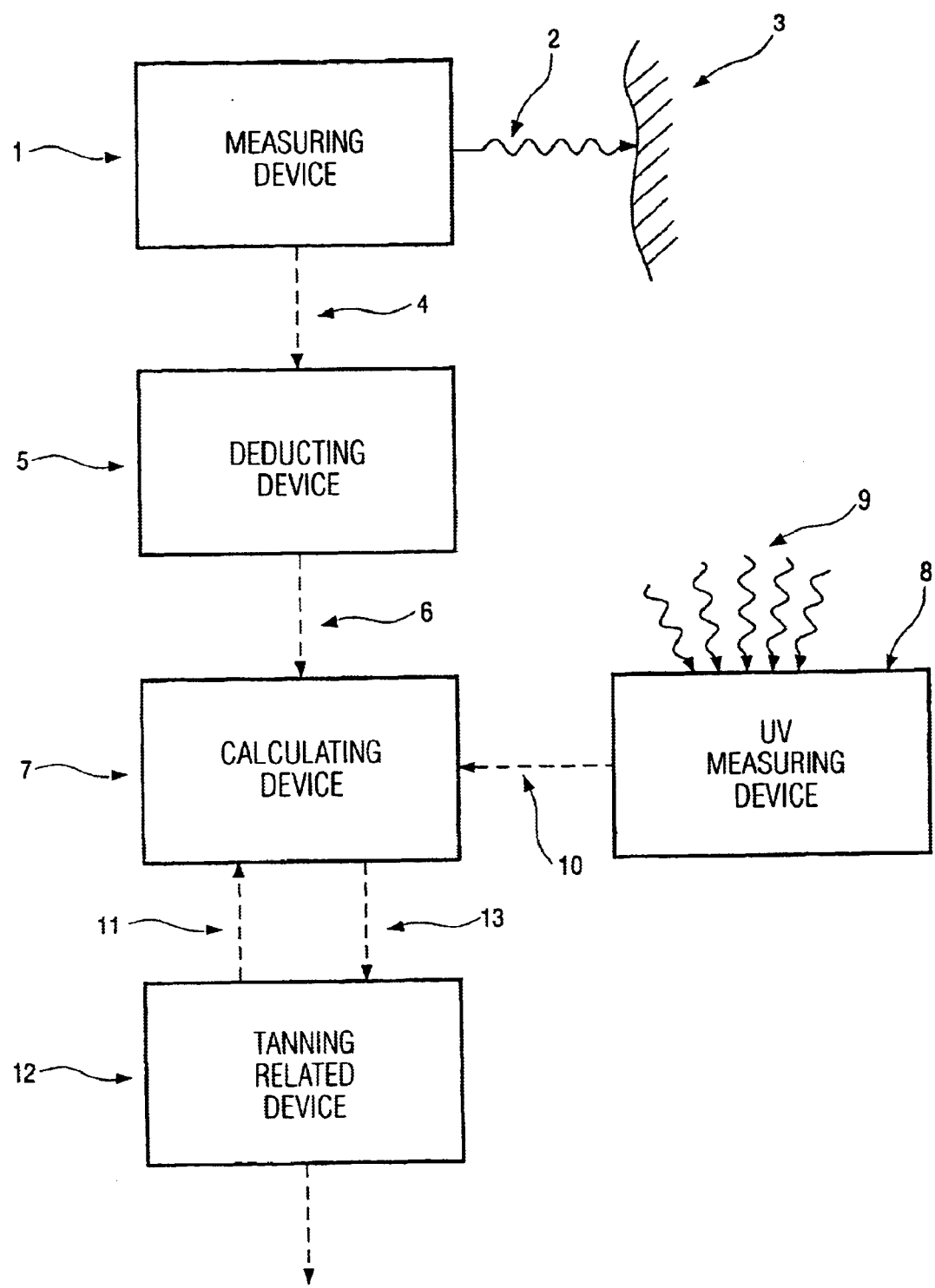
FIG. 1 is a block diagram of a preferred embodiment of the invention.

FIG. 1 diagrammatically shows a measuring device 1 capable of carrying out a non-invasive measurement 2 on skin 3, correlated to the MED. The measuring device 1 sends a signal 4, representing the measured value, to a deduction device 5. The deduction device 5, having knowledge about the correlation between the measured value and the MED, deduces the MED from the signal 4. A signal 6 representing the MED is sent to a calculation device 7, preferably a microprocessor. Optionally, a UV-measuring device 8 is provided for measuring the UV radiation level 9, for example coming from the sun or from a solarium lamp. A signal 10 representing the UV radiation level 9 is also sent to the calculation device 7. On the basis of signals 6 and 10 the calculating device is able to calculate a safe sunbathing time using the formula: safe sunbathing time=MED ($J\ m^{-2}$) divided by the (measured) UV radiation level ($J\ m^{-2}S^{-1}$).

In the absence of a UV-measuring device 8, the calculation device may also use a preprogrammed value for the UV radiation level or a signal 11 coming from the tanning-related device 12, for example a solarium. A signal 13 representing the safe sunbathing time is sent by the calculation device 7 to the tanning-related device 12. This tanning-related device 12 may be, for example, a solarium, as was noted above, having a switch for turning on both the solarium itself and a timer, which switch turns off the solarium automatically as soon as a time period corresponding to the safe sunbathing time has elapsed. Alternatively, the tanning-related device may be a dosimeter, for example in the form of a solar watch which gives a warning signal, for example a light or sound signal, as soon as a time period corresponding to the safe sun-bathing time has elapsed.

Figure 2:
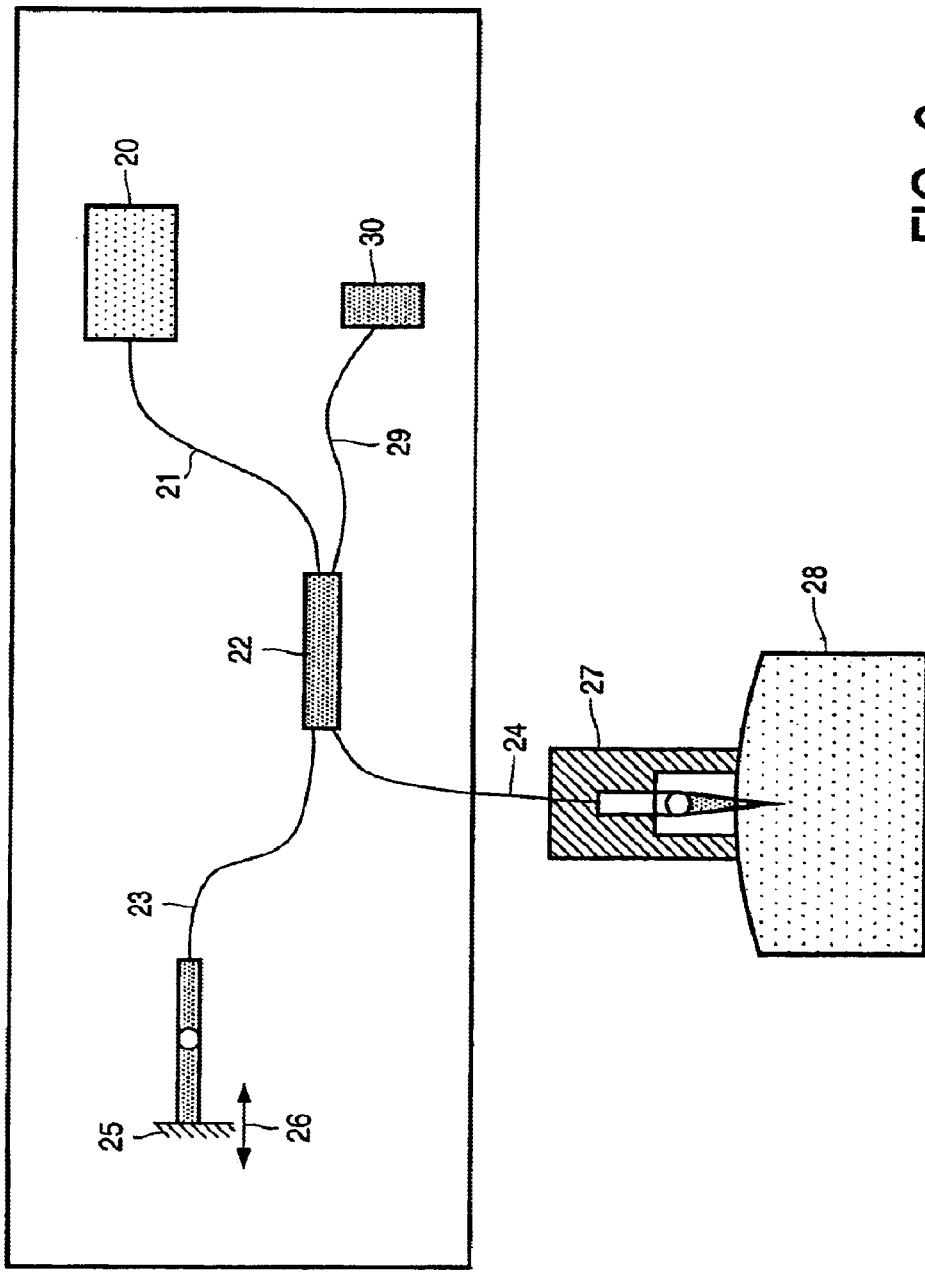
FIG. 2 is a diagrammatic view of a measuring device.
Figure 3:
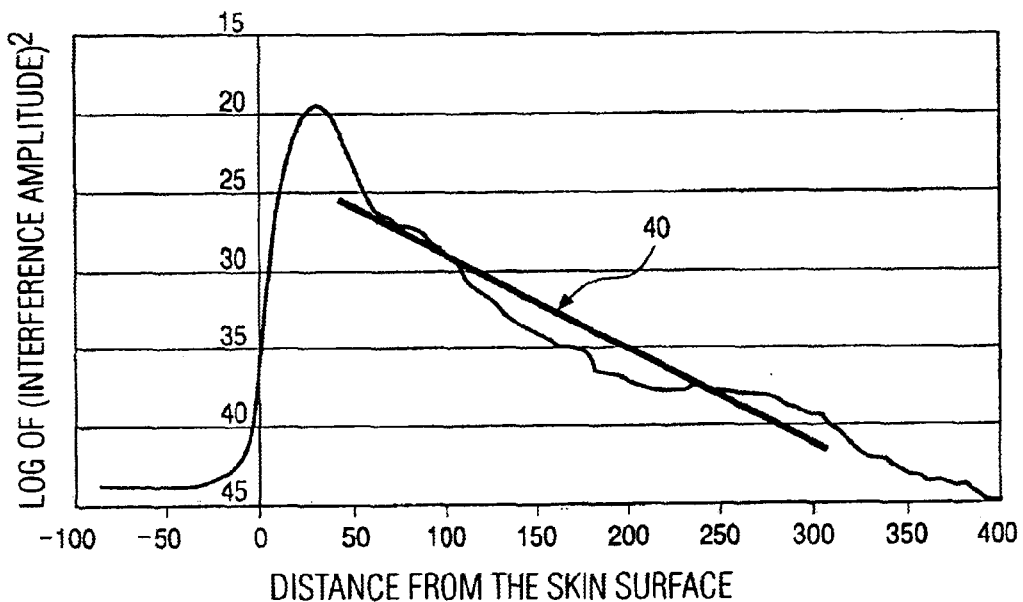
FIG. 3 is a diagram illustrating the attenuation in the skin.

FIG. 2 diagrammatically shows the optical coherence domain reflectometry (OCDR) technique which is able to measure the light attenuation in the skin non-invasively. Light emitted by a light source 20 is sent through a fiber 21. In a fiber coupler 22 the light is split into two equal portions which are sent through fibers 23 and 24, respectively. At the free end of fiber 23 a mirror 25 is located which is movable in the direction of arrow 26. The mirror 25 reflects the light back through the fiber 23 to the fiber coupler 22. At the free end of the fiber 24 a probe 27 is located which is placed on skin 28. Like the mirror 25, the skin 28 also reflects the light, this time coming back through the fiber 24 to the fiber coupler 22. The light reflected by the mirror 25 through the fiber 23 and the light reflected by the skin 28 through the fiber 24 is sent through the fiber 29 to a detector 30. Given the fact that the incoming and reflected light through the fiber 23 has the same path length as the incoming and reflected light through the fiber 24, interference will take place which can be detected by the detector 30. By moving the mirror 25 in direction 26, one can measure the light reflection in different positions below the skin surface. As may be expected, the reflections will be less due to absorption and scattering of light as positions are located deeper under the skin surface. This attenuation is shown in FIG. 3 in which the distance from the skin surface is plotted horizontally and the logarithm of the squared interference amplitude vertically. This relation can be approximated by a straight linear line having a slope 40. This slope 40 is a measure for the MED.

Figure 4:
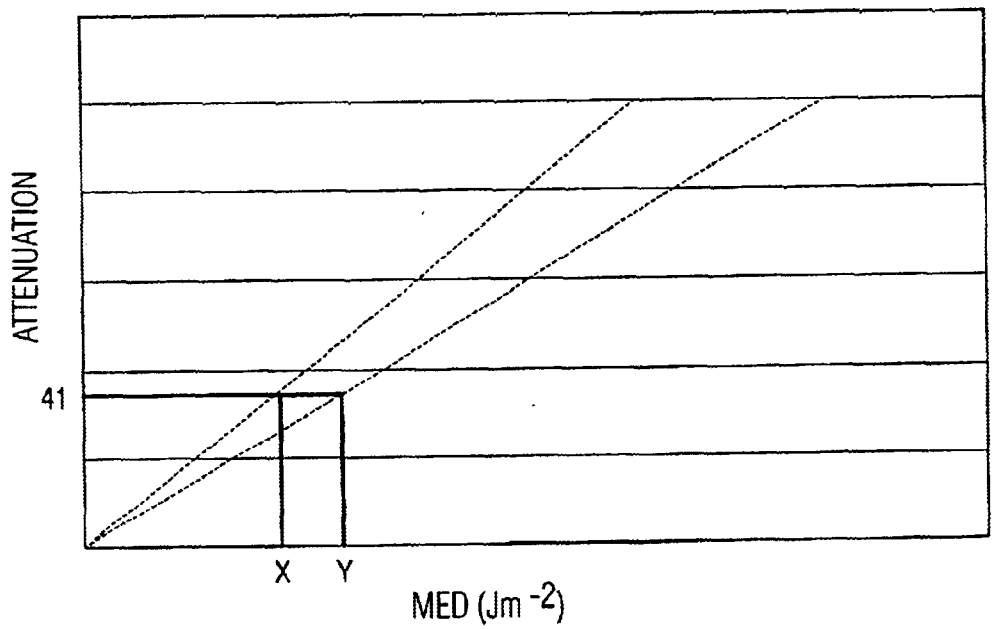
FIG. 4 is a diagram illustrating the correlation between the MED and the attenuation.

In FIG. 4, the MED is plotted horizontally and the attenuation represented by the slope of line 40 vertically. The attenuation and the MED were found to correlate to each other. Having established the attenuation 41 corresponding to slope 40 one can predict with a reasonable amount of certainty that the MED will have a value between X and Y. The MED can be non-invasively determined in this way and used for controlling a tanning-related device such as a solarium or a dosimeter.

What is claimed is:

1. Method comprising steps
   A) determining a quantity related to a person's personal minimal erythema dose (MED),
   B) using the quantity for the input of a tanning related device thus influencing its operation, and comprising for the purpose of step A), steps C) non-invasively measuring a feature of a person's skin related to the person's personal MED, and D) electronically deducting the person's personal MED from the measured feature, wherein the feature of the person's skin which is measured by the measuring means is light attenuation.

2. Device for use with a tanning related device comprising measuring means for non-invasively measuring a feature of a person's skin related to the person's personal minimal erythema dose (MED), deduction means for deduction of the person's personal MED from the measured feature and communicating means for electronically communicating a signal representing the deducted MED to a tanning related device, wherein the feature of the person's skin which is measured by the measuring means is light attenuation.

3. Device according to claim 2 wherein the light attenuation in the person's skin is measured by applying optical coherence tomography, optical coherence-domain reflectometry or spatially resolved diffuse reflectance spectroscopy.

4. Device according to claim 2 wherein in addition to the feature of light attenuation, the feature of light reflection of the person's skin is measured by the measuring means.

5. Device according to claim 2 characterized by calculating means for calculating a safe sun bathing time on the basis of the MED and of a relevant solar UV radiation level.

6. Device according to claim 5 characterized by UV measuring means for measuring the relevant solar UV radiation level.

7. Device according to claim 5 characterized by a timer for giving a warning signal, for instance a sound or light signal, as soon as a time period corresponding to the safe sun bathing time has lapsed.

8. Device according to claim 2, wherein the tanning related device is a solarium.

* * * * *